United States Patent [19]

Moss

[11] 3,987,547

[45] Oct. 26, 1976

[54] ORTHODONTIC APPLIANCE AND METHOD OF ORTHODONTIC TREATMENT

[76] Inventor: Dan Moss, P.O. 1108, Cedar City, Utah 84720

[22] Filed: Apr. 3, 1975

[21] Appl. No.: 564,890

[52] U.S. Cl. .................................................. 32/14 E
[51] Int. Cl.² .......................................... A61C 7/00
[58] Field of Search ................ 32/14 A, 14 R, 14 C, 32/14 B, 14 D, 14 E

[56] References Cited
UNITED STATES PATENTS

| | | | |
|---|---|---|---|
| 2,318,001 | 5/1943 | Linde | 32/14 E |
| 2,705,367 | 4/1955 | Benke | 32/14 A |
| 3,487,545 | 1/1970 | Weissman | 32/14 A |

OTHER PUBLICATIONS

"Space Maintainers Cat.," Space Maintainers Lab., Panorama City, Calif., pp. 8–12, Apr. 1, 1968.

Primary Examiner—Louis G. Mancene
Assistant Examiner—Jack Q. Lever

[57] ABSTRACT

The orthodontic appliance comprises a palatal appliance having upper and lower surfaces which is adapted to be inserted into the patient's mouth with the upper surface in surface contact with the palate. A plurality of wire members are attached to the lower surface of the palatal appliance. The wire members each have three sections which respectively project from the lower surface, across the dental arch and to the outside thereof when the palatal appliance is inserted into the mouth of the patient. An arch wire having first and second ends is attached to orthodontic brackets that have been bonded to the patient's teeth. The ends of the arch wire are activated by respectively coupling them to the third section of a pair of the wire members. The coupling of the ends of the arch wire to the wire members obviates the need for buccal tubes to activate the arch wire.

The arch wire comprises a section of wire having built-in occulsalgingival torque when the ends of the arch wire are activated by attachment to the appliance discussed above or to a conventional buccal tube.

The method of the present invention consists of three phases of treatment. The first phase comprises attaching a plurality of conventional orthodontic brackets to the teeth, attaching a first arch wire to the orthodontic bracket without activating the ends of the arch wire by coupling them to teeth and then applying conventional correction forces to the teeth. The second phase comprises removing the first arch wire, attaching a second arch wire, activating the ends of the second arch wire by coupling its ends with the appliance discussed above, and then applying conventional correction forces to the teeth. The third phase comprises removing the second arch wire and attaching a third arch wire as described above which has built-in torque when the ends of the third arch wire are activated by coupling with the appliance discussed above and then applying correction forces until the orthodontic treatment is completed.

18 Claims, 5 Drawing Figures

ORTHODONTIC APPLIANCE AND METHOD OF ORTHODONTIC TREATMENT

BACKGROUND OF THE INVENTION

1. Field of the Invention

The invention relates to orthodontic appliances and methods of orthodontic treatment. More particularly, the invention relates to orthodontic appliances and methods of orthodontic treatment which do not utilize buccal tubes to activate the arch wire. The invention also relates to an arch wire having built-in occulsal-gingival torque which is activated by attachment of the ends of the arch wire to either the appliance discussed above or to a conventional buccal tube.

2. Description of the Prior Art

Heretofore, orthodontic arch wires have been activated by attachment of the ends of the arch wire to a pair of buccal tubes which are connected to the teeth by orthodontic bands. It has been found that the speed of movement of malposed teeth is limited by multiple band and bracket interferences and mastication orthodontic forces.

Prior to the use of the arch wire of the present invention, orthodontists corrected cuspid angulation by an auxiliary bend in the arch wire.

SUMMARY OF THE INVENTION

A class of orthodontic problems known as Class 1 usually requires only straightening of one or two teeth. A high percentage of these Class 1 problems do not require any posterior movement of the teeth. These problems can be routinely corrected by using the present invention by a general dentist who has a limited amount of formal orthodontic training. It has been found that the general dentist using the present invention which has been constructed by a special laboratory and using direct bonding techniques of attaching orthodontic brackets to the teeth is able to perform the aforementioned corrections with as little as eight hours of formal training.

The present invention obviates the need for using posterior bands and the concomitant inventory requirements. By using a special orthodontic appliance laboratory to construct orthodontic appliances constructed according to the present invention, the dentist's or orthodontist's investment in office supplies is reduced.

Accordingly, the present invention permits the general dentist to perform Class 1 orthodontic corrections in a professional manner with approximately 8 hours of formal training.

The disadvantages and limitations of the prior art are obviated by the present invention which provides an orthodontic appliance and method of orthodontic treatment which obviates the activating of the arch wire by attachment to buccal tubes which are connected to orthodontic bands encircling the teeth.

The appliance of the present invention includes a palatal appliance, having upper and lower surfaces, which is adapted to be inserted into the patient's mouth with the upper surface in surface contact with the patient's palate and a plurality of wire members which are attached to and project from the lower surface of the palatal appliance across and to the outside of the dental arch when the appliance is inserted into the patient 'mouth. The wire members are symetrically mounted on the bottom surface of the palatal appliance. A ball clasp is mounted on the end of each of the sections of the wire members which extend outside of the dental arch when the appliance is inserted in the patient's mouth.

Activation of the appliance is produced by bonding orthodontic brackets to the teeth, attaching an arch wire having first and second ends to the orthodontic brackets and coupling the ends of the arch wire to a pair of the ball clasps disposed in proximity to the ends of the arch wire.

The method of orthodontic treatment of the present invention comprises three phases including the steps of bonding a plurality of the orthodontic brackets to the teeth of a patient, attaching a first arch wire having first and second ends to the orthodontic brackets without activating the ends, inserting the appliance described above into the patient's mouth, applying conventional correction forces to the teeth, removing the first arch wire, attaching a second arch wire having first and second ends to the orthodontic brackets, activating the ends of the second arch wire by coupling them to a pair of ball clasps disposed adjacent to the ends of the second arch wire, applying conventional forces to the teeth, removing the second arch wire, attaching a third arch wire having first and second ends to the orthodontic brackets, activating the arch wire to produce built-in torque by attaching the first and second ends of the arch wire to a pair of ball clasps disposed adjacent to the ends of the arch wire and applying conventional correction forces until completement of the orthodontic treatment.

Phases two and three may also be used to correct an extraction case, a diastema case and Class 3 malocculsions.

An arch wire constructed according to the present invention is used as the third arch wire in the process summarized above and as an arch wire in orthodontic appliances using buccal tubes to activate the ends of the arch wire. The arch wire has a pair of helical springs formed integrally from the arch wire for producing torque in the occulsal-gingival direction when the ends of the arch wire are activated including a cuspid angulation due to the activated wire.

DETAILED DESCRIPTION OF THE INVENTION

Figure 1:
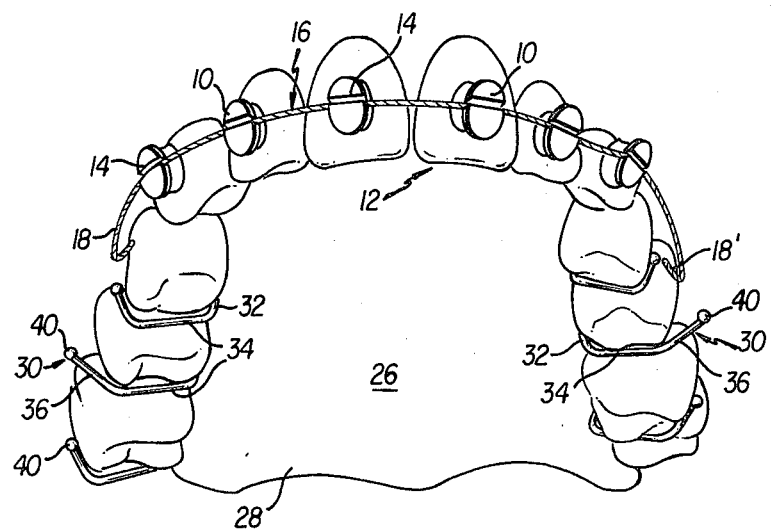
FIG. 1 is an isometric view illustrating the appliance used in the first phase of the method of orthodontic treatment of the present invention.

The first phase of the method of orthodontic treatment of the present invention is explained as follows with reference to FIG. 1. A plurality of orthodontic brackets 10 are preferably directly bonded by dental adhesives to the teeth 12 undergoing orthodontic treatment. The orthodontic brackets are preferably bonded to the teeth by a dental adhesive sold by Lee Pharmaceuticals under the trademark GENIE. Each bracket 10 includes a conventional arch wire slot 14 and a ligature undercut (not shown) extending underneath the periphery of the front surface of the bracket. The preferred type of orthodontic bracket is described in U.S. patent application Ser. No. 467,675. A first arch wire 16, having ends 18 and 18', is disposed in the arch wire slot 14 of each bracket and secured to the bracket 10 by a conventional ligature (not shown). The arch wire 16 may be either a multistrand or alligator wire of well known construction. During phase one, the palatal appliance 24 is inserted into the patient's mouth with the upper surface (not shown) in contact with the patient's palate. The upper surface is shaped to conform to patient's palate. A plurality of wire members 30 project from the lower surface 28 of the palatal appliance 24. The wire members 30 are embedded in the palatal appliance 24. The palatal appliance 24 may be constructed from any well known dental plastic. However, acrylic resins are the preferred plastic. The wire members are symetrically disposed with respect to a plane bisecting the appliance as viewed from the front of the patient's mouth. Each of the wire members 30 consists of three sections, 32, 34 and 36. The first section 32 projects from the lower surface 29 in proximity to dental arch 38. The second section 34 includes a bend which straddles the dental arch 38 when the appliance 24 is inserted into the patient's mouth. Each of the sections 36 ends in a ball clasp 40 which is used for coupling the appliance 24 to the ends of the arch wire used in the second and third phases of orthodontic treatment which are described below.

The first phase of orthodontic treatment of the present invention is completed by applying conventional correction forces to the teeth 12 without activating the ends 18 and 18' of the arch wire 16 by coupling them to the teeth. During this phase of orthodontic treatment, requisite bends in the arch wire 16 are made to apply conventional correction forces to the teeth 12 to produced leveling of the teeth and to unrotate the teeth to line up the brackets 10.

Figure 2:
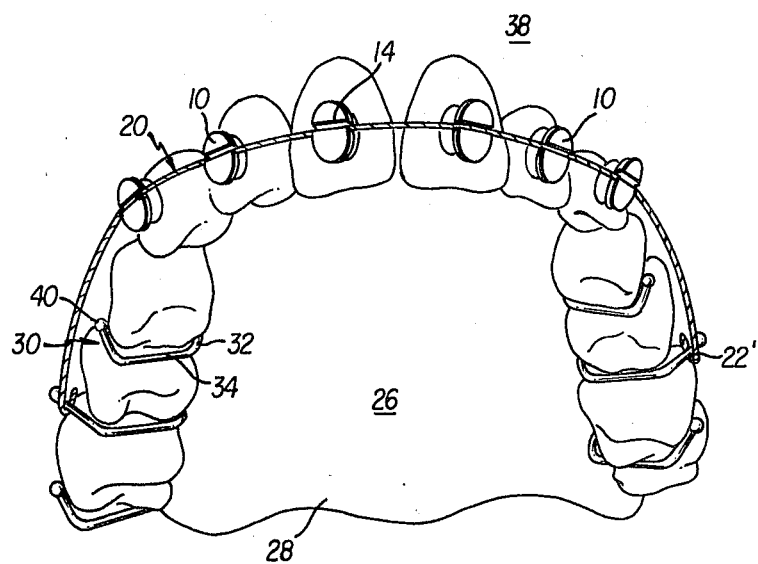
FIG. 2 is an isometric view illustrating the appliance used in the second phase of the method of orthodontic treatment of the present invention.

The second phase of the orthodontic treatment is explained as follows with reference to FIG. 2. At the inception of the second phase of treatment, the first arch wire 16, illustrated in FIG. 1, is removed by detaching the ligatures. A second arch wire 20 is inserted in the arch wire slots 14 of brackets 10 and attached thereto by ligatures (not shown). Arch wire 20 is preferrably a round wire of 0.016 inch diameter. The ends 22 and 22' of arch wire 20 are activated in the second phase of orthodontic treatment by attachment to the ball clasps 40 which are part of the palatal appliance 24 described above.

The activation of the second arch wire 20 in the second phase of orthodontic treatment is completed by hooking the ends 22 and 22' of arch wire 20 over a pair of ball clasps 40 disposed in proximity to the ends of the arch wire 20.

Figure 3:
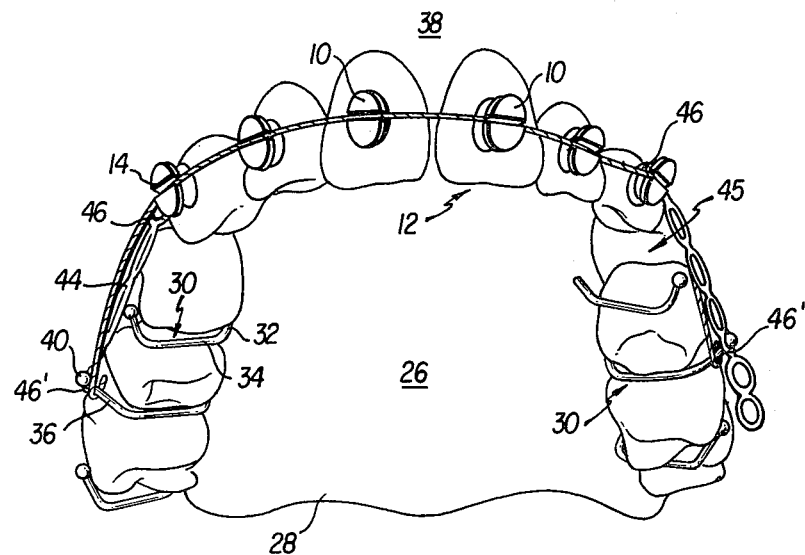
FIG. 3 is an isometric view illustrating the appliance used in the second phase of the method of orthodontic treatment of the present invention for correcting an extraction case.

FIG. 3 illustrates the treatment in phase two of an extraction case. In this form of treatment an elastic 44 having ends 46 and 46' is coupled to a bracket 10 which is attached to the tooth 12 which is to be moved into the extraction area 45 and to a ball clasp 40 disposed adjacent to the extraction area 45.

Figure 4:
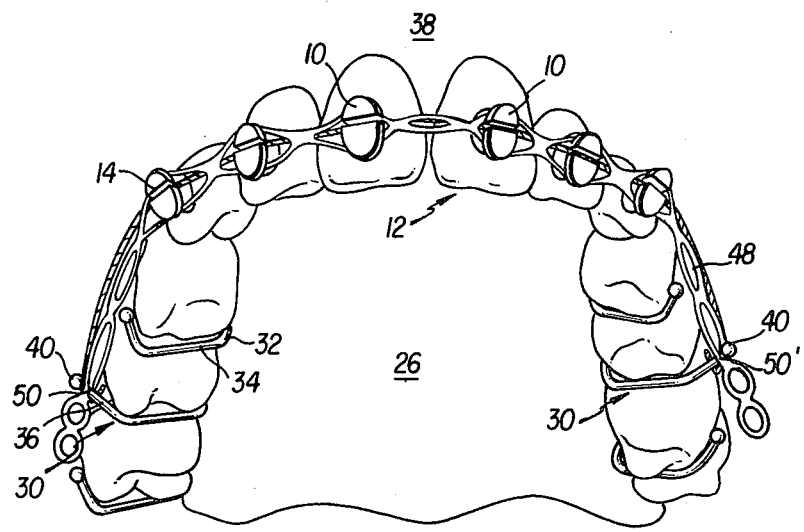
FIG. 4 is an isometric view illustrating the appliance used in the second phase of the method of orthodontic treatment of the present invention for correcting a diastema case.

FIG. 4 illustrates the treatment in phase two of a case of diastema. In this form of treatment, an elastic 48 is attached to a pair of the ball clasps 40 at its ends 50 and 50' and to orthodontic brackets 10 at intermediate points. The constriction force exerted by the elastic 48 pulls the dental arch 38 together.

After activation of the ends 22 of the arch wire 20, the second phase of orthodontic treatment is completed by applying conventional correction forces to the teeth 12 to improve rotation and leveling and to close spacing.

Figure 5:
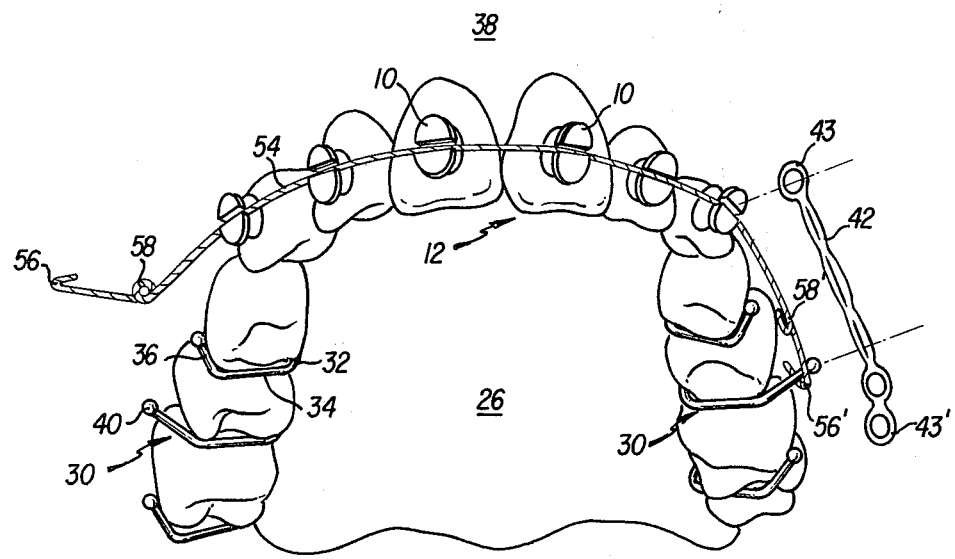
FIG. 5 is an isometric view illustrating the appliance and arch wire of the present invention used in the third phase of the method of orthodontic treatment of the present invention.

The third phase of orthodontic treatment is explained as follows with reference to FIG. 5. The third phase of treatment is begun by removing the second arch wire 20 by detaching the ligatures and attaching a third arch wire 54 to the orthodontic brackets 10 by ligatures (not shown). The arch wire 54 has a pair of ends 56 and 56' which are attached to ball clasps 40 in the same way described with reference to FIG. 2. A pair of helical springs 58 are integrally formed from the arch wire 20. The axis of the helical springs 58 is disposed generally perpendicular to the dental arch 38. When the ends 56 and 56' of the arch wire 54 are activated by coupling them to ball clasps 40, arch wire 54 produces a built-in torque in the occulsal-gingival direction. The degree of built-in torque may be changed by design techniques well known to those skilled in the art. The built-in torque in arch wire 54 facilitates the application of torque to the anterior teeth without requiring auxiliary bends in the arch wire.

when it is desired to produce labial-lingual torquing of the anterior teeth 12, an elastic 42 having ends 43 and 43' is attached between the most posteriorly located anterior tooth to be torqued and a ball clasp 40.

For Class 3 malocculsion, the method of orthodontic treatment of the present invention may be initiated by starting with the second or third phase of orthodontic treatment of the present invention to produce expansion or labial positioning of the anterior teeth due to the activation of the torquing without the elastic chain tied back to the ball clasps.

The third phase of orthodontic treatment is completed by application of conventional correction forces to the teeth 12.

It has been found that the arch wire 44 may be used in either phase of three of the orthodontic methods of treatment of present invention or in conjunction with conventional orthodontic treatment methods which use buccal tubes to activate the ends of the arch wire.

While the invention has been described in its preferred form, it should be readily apparent to those skilled in the art that numerous modifications may be made thereto without departing from the spirit and scope of the invention. It is intended that these modifications fall within the scope of the appended claims.

What is claimed is:

1. An orthodontic appliance for insertion into the mouth of a patient in surface contact with the palate and adjacent to the dental arch comprising:
    a palatal appliance having upper and lower surfaces, said appliance being inserted into the mouth with the upper surface in contact with the palate;
    b. a plurality of wire members, each wire member having a first section attached to said palatal appliance and projecting from said lower surface; a second section straddling the dental arch and a third section extending outside of the dental arch;

c. a plurality of orthodontic brackets each attached to different teeth disposed in the mouth of a patient, said brackets each having an arch wire slot; and d. an arch wire having first and second ends being respectively coupled to first and second third sections of said wire members by a pair of attachment means, said arch wire being disposed in said arch wire slots.

2. In an orthdontic appliance as recited in claim 1 wherein said pair of attachment means comprises:
 a. first and second ball clasps respectively attached to the end of said first and second third sections of said wire members; and
 b. first and second bend end sections disposed at the first and second ends of said arch wire, said first and second end sections being respectively coupled to said ball clasps.

3. In an orthodontic appliance as recited in claim 2 further comprising:
 a. an elastic having first and second ends, said first end being attached to an orthodontic bracket which is coupled to a tooth disposed adjacent to an extraction area to which it is desired to move the tooth, said second end being coupled to one of said ball clasps.

4. In an orthodontic appliance as recited in claim 2 further comprising:
 a. first and second elastics each having first and second ends, said first ends of said first and second elastics being respectively attached to different orthodontic brackets, said second ends being respectively attached to first and second ball clasps.

5. In an orthodontic appliance as recited in claim 2 further comprising:
 a. an elastic having first and second ends and an intermediate section, said first end being coupled to a ball clasp disposed on one side of a plane bisecting a patient's mouth as viewed from the front, said second end being coupled to a ball clasp disposed on the other side of the plane bisecting the patient's mouth as viewed from the front and said intermediate section being attached to a plurality of orthodontic brackets attached to the anterior portion of the dental arch.

6. In an orthodontic appliance as recited in claim 2 wherein said arch wire comprises:
 a. a wire not having built-in torque when activated by coupling said first and second ends respectively to said first and second ball clasps.

7. In an orthodontic appliance as recited in claim 2 wherein said arch wire comprises:
 a. a wire having built-in torque when activated by coupling said first and second ends respectively to said first and second ball clasps.

8. In an orthodontic appliance as recited in claim 7 wherein:
 a. said torque acts in the occulsal-gingival direction.

9. In an orthodontic appliance as recited in claim 7 wherein:
 a. said torque is produced by a pair of springs formed integrally from said wire, each spring comprising at least one helical loop.

10. An arch wire for use in orthodontic treatment comprising:
 a. a generally U-shaped section of wire having first and second ends, said section of wire being shaped to conform to the arch of a patient undergoing orthodontic treatment,
 b. a plurality of orthodontic brackets each attached to different teeth of the patient, said U-shaped section of wire being coupled to said plurality of orthodontic brackets.
 c. means integrally formed from said section of wire for producing torque in the occulsal-gingival direction when said ends are activated.

11. An arch wire as recited in claim 10 wherein said means comprises:
 a. a pair of springs integrally formed from said section of wire.

12. An arch wire as recited in claim 11 wherein said springs each comprise:
 a. at least one helical loop of wire.

13. A method of orthodontic treatment comprising the steps:
 a. attaching orthodontic brackets to the teeth of a patient undergoing orthodontic treatment;
 b. attaching a first arch wire having first and second ends to said orthodontic brackets;
 c. inserting a palatal appliance having upper and lower surfaces into the mouth of the patient, the upper surface of said palatal appliance being in surface contact with the palate of the patient, said palatal appliance having a plurality of wire members, each wire member having a first section attached to said lower surface and projecting from said lower surface, a second section straddling the dental arch of said patient when the palatal appliance is inserted into the patient's mouth and a third section extending outside of the dental arch when the palatal appliance is inserted into the patient's mouth; and
 d. applying correctional forces to said teeth to which said orthodontic brackets are attached without activating said arch wire by coupling said ends to said teeth.

14. A method as recited in claim 13 further comprising the steps:
 a. detaching said arch wire from said orthodontic brackets;
 b. attaching a second arch wire having first and second ends to said orthodontic brackets, said arch wire not having built-in torque when said ends are activated;
 c. coupling two of the third sections of said wire members respectively to said first and second ends of said second arch wire to activate said arch wire; and
 d. applying correction forces to the teeth.

15. A method as recited in claim 14 further comprising the steps:
 a. a detaching said second arch wire from said orthodontic brackets;
 b. decoupling the first and second ends of said arch wire from said respective third sections;
 c. attaching a third arch wire having first and second ends to said orthodontic brackets, said arch wire having built-in torque when said ends are activated; and
 d. coupling two of the third sections of said wire members respecitvely to said first and second ends of said third arch wire to activate said third arch wire.

16. A method as recited in claim 14 further comprising the steps:

a. attaching first and second elastics each having first and second ends respectively so that the first ends of said first and second elastics are attached to orthodontic brackets disposed respectively in proximity to the first and second ends of said second arch wire and so that the second ends of said first and second elastics are attached to two of the third sections of said wire members.

17. A method as recited in claim 14 further comprising the steps:
   a. attaching an elastic having first and second ends so that the first end of said elastic is attached to an orthodontic bracket connected to a tooth disposed adjacent to an extraction area to which the tooth is to be moved, and the second end is attached to a third section of said wire member disposed in proximity to said extraction area.

18. A method recited in claim 14 further comprising the steps:
   a. attaching an elastic having first and second ends so that the first end is attached to a third section of one of said wire members disposed on one side of a plane bisecting a patient's mouth as viewed from the front, the second end is attached to a third section of one of said wire members disposed on the other side of a plane bisecting the patient's mouth viewed from the other side and an intermediate section is attached to a plurality of orthodontic brackets which are bonded to the anterior teeth.

* * * * *